United States Patent
Kim et al.

(10) Patent No.: US 6,656,116 B2
(45) Date of Patent: Dec. 2, 2003

(54) APPARATUS AND METHOD FOR PERCEIVING PHYSICAL AND EMOTIONAL STATE

(75) Inventors: Jay-woo Kim, Kyungki-do (KR); Seok-won Bang, Kyungki-do (KR); Jeong-hwan Kim, Seoul (KR); Hyoung-ki Lee, Kyungki-do (KR)

(73) Assignee: Samsung Electronics Co. Ltd. (KR)

( * ) Notice: Subject to any disclaimer, the term of this patent is extended or adjusted under 35 U.S.C. 154(b) by 0 days.

(21) Appl. No.: 09/931,767

(22) Filed: Aug. 20, 2001

(65) Prior Publication Data

US 2003/0078505 A1 Apr. 24, 2003

(30) Foreign Application Priority Data

Sep. 2, 2000 (KR) .......................... 2000-51821
Feb. 7, 2001 (KR) .......................... 2001-5943

(51) Int. Cl.[7] .............................................. A61B 5/00
(52) U.S. Cl. ........................................................ 600/300
(58) Field of Search .............................. 600/300, 301, 600/26–28, 547, 549; 128/903, 905, 897, 898, 920, 923–925

(56) References Cited

U.S. PATENT DOCUMENTS

| | | | |
|---|---|---|---|
| 4,683,891 A | | 8/1987 | Cornellier et al. |
| 5,367,454 A | | 11/1994 | Kawamoto et al. |
| 5,507,291 A | | 4/1996 | Stirbl et al. |
| 5,601,090 A | * | 2/1997 | Musha .................. 128/925 |
| 5,676,138 A | * | 10/1997 | Zawilinski ............ 600/301 |
| 5,741,217 A | * | 4/1998 | Gero ..................... 600/547 |
| 5,862,803 A | * | 1/1999 | Besson et al. ........ 128/903 |
| 5,974,262 A | * | 10/1999 | Fuller et al. ......... 600/301 |
| 6,021,346 A | * | 2/2000 | Ryu et al. ............. 600/300 |
| 6,026,322 A | | 2/2000 | Korenman et al. |
| 6,131,579 A | * | 10/2000 | Thorson et al. ...... 600/549 |
| 6,190,314 B1 | * | 2/2001 | Ark et al. ............. 600/300 |
| 6,293,904 B1 | * | 9/2001 | Blazey et al. ........ 600/26 |
| 6,375,622 B1 | * | 4/2002 | Kao et al. ............. 600/300 |

FOREIGN PATENT DOCUMENTS

| | | |
|---|---|---|
| KR | 1997-14722 | 4/1997 |
| KR | 1999-63100 | 7/1999 |

OTHER PUBLICATIONS

Introduction to Biomedical Equipment Technology ($2^{nd}$ Edition), pp 25–37, 163–177 and 207–209.

(List continued on next page.)

*Primary Examiner*—Eric F. Winakur
*Assistant Examiner*—David J. McCrosky
(74) *Attorney, Agent, or Firm*—Burns, Doane, Swecker & Mathis, L.L.P.

(57) ABSTRACT

An apparatus and method for perceiving a physical and emotional state, which allows easy attachment to and detachment from a human body, and through which a bio-signal is simply detected, are provided. The apparatus includes a bio-signal detection part attached to a predetermined portion of a body for performing analog signal processing on at least one bio-signal detected from the body and outputting the processed bio-signal, and a bio-signal recognizing part for performing digital signal processing on the processed bio-signal received from the bio-signal detection part, perceiving the physical and emotional state from the result of the digital signal processing, and representing the physical and emotional state. Accordingly, the apparatus can be conveniently attached to a predetermined portion of a user's body, a bio-signal transmitted wirelessly or through a wire can be easily detected, a physical and emotional state which is perceived based on the detected bio-signal can be reported to the user, and a rapidly changing emotional state or an emotional state which remains for a long time can be perceived in real time.

46 Claims, 9 Drawing Sheets

OTHER PUBLICATIONS

Bosch Automotive Electric–Electronic Systems Handbook, 1995, Robert Bentley, 3rd Edition, Cambridge, MA, pp 107–111.

Principles of Biomedical Instrumentation and Measurement, pp. 100–107 and 113–122.

Don C. Fowles et al., "Publication Recommendation for Electrodermal Measurements", pp 232–239, May 1981, The Society for Psychophysiological Research, Inc.

Korean language version of Chapter 5, "Introduction to Biomedical Equipment Technology" ($2^{nd}$ Edition), 1996, pp 171–216.

Joseph J. Carr and John M. Brown, Chapter 5, "Introduction to Biomedical equipment Technology" (2nd Edition) 1993, pp 123–127.

A. W. Frey et al., "The Respiratory Sinus Arrhythmia as a Function of Breathing Frequency Revisited", Computers in cardiology 1994, pp 41–44.

Pei Z. Zhang et al., "Respiration Response Curve Analysis of Heart Rate Variability", Apr. 1997, pp 321–325, IEEE Transactions on Biomedical Engineering, vol. 44, No. 4.

* cited by examiner

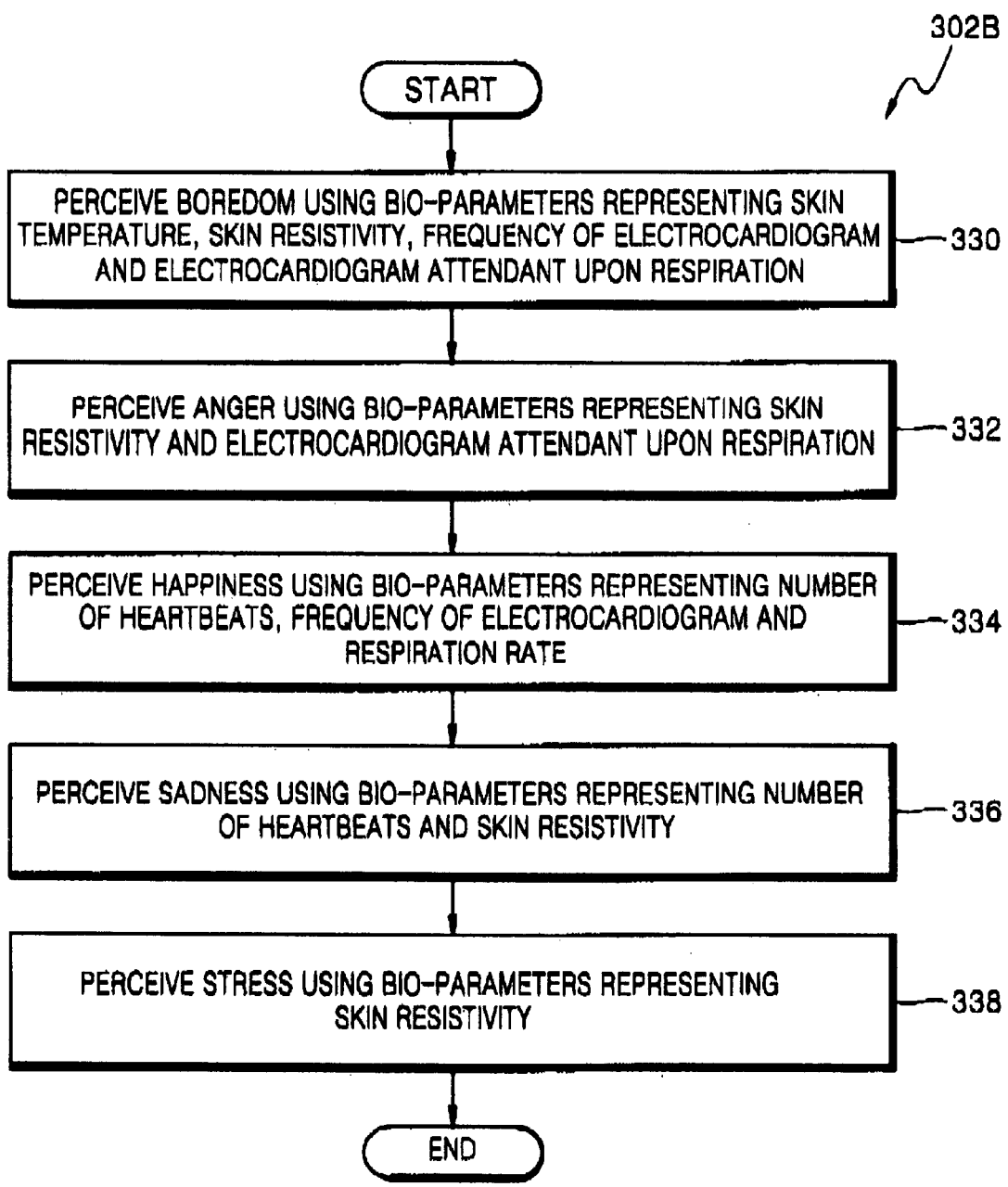

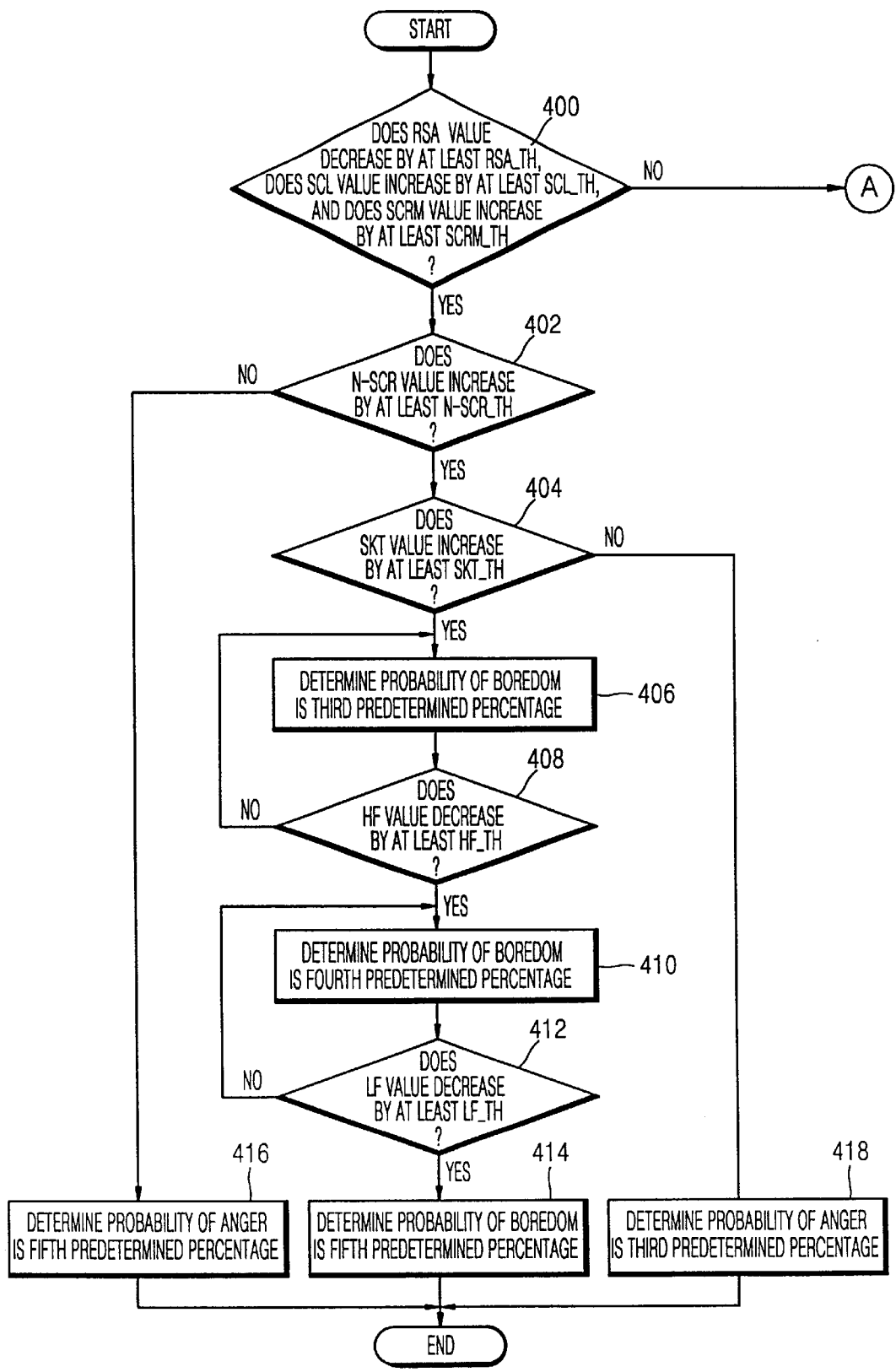

APPARATUS AND METHOD FOR PERCEIVING PHYSICAL AND EMOTIONAL STATE

BACKGROUND OF THE INVENTION

1. Field of the Invention

The present invention relates to the use of a bio-signal, and more particularly, to an apparatus and method for perceiving a physical and emotional state using a bio-signal.

2. Description of the Related Art

Detecting or measuring a human bio-signal was studied and applied mainly in medicine in the initial stage. That is, in order to check the health condition of a patient or treat patients referring to blood pressure or a pulse rate, a bio-signal detected or measured is used. Recently, bio-signals are applied in the field of man-machine interfacing for understanding a person's emotions, as well as in the medicine. Particularly, it is considered to be essential to be able to perceive a person's emotions using a bio-signal in order to enable more convenient and familiar communication between man and machine. Accordingly, a variety of apparatuses for detecting or measuring a bio-signal (or a physiological signal) and using it have been developed.

An apparatus for measuring bio-information using an ear-receiver type Photo-electric pulse PlethysmoGraph (PPG) sensor, which is disclosed in Korean Patent Publication No. 1999-63100, and a real time bio-signal monitoring system using wireless communication networks, which is disclosed in Korean Patent Publication No. 1997-14722, are conventional portable bio-signal measuring apparatuses. However, such conventional apparatuses are disadvantageous in that they are not easy to attach to a human body, or in that it is inconvenient for people to move with them attached.

Among conventional bio-signal measuring apparatuses, emotion perceiving apparatuses are disclosed in U.S. Pat. No. 5,507,291 entitled "Method and an Associated Apparatus for Remotely Determining Information as to Person's Emotional State" and U.S. Pat. No. 5,367,454 entitled "Interactive Man-Machine Interface for Simulating Human Emotions". However, these conventional apparatuses have the same problems described above.

When conventional emotion perceiving apparatuses are used for perceiving a person's emotions, the person should make an artificial effort, for example, the person should always direct his/her face toward a camera so that his/her facial expression can be seen well, or the person should speak words expressing his/her emotions. Accordingly, the person's emotions cannot be naturally transmitted to such conventional apparatuses. In addition, conventional emotion perceiving apparatuses have many restrictions, for example, they may not perceive a specific emotion and they infer an emotion from only reactions to previously and artificially made-up emotional stimuli.

SUMMARY OF THE INVENTION

To solve the above problems, it is a first object of the present invention to provide an apparatus for perceiving a physical and emotional state, which is easily attached to and detached from a human body and through which a bio-signal is simply detected.

It is a second object of the present invention to provide a method for perceiving a physical and emotional state using the above apparatus for perceiving a physical and emotional state.

It is a third object of the present invention to provide a method for perceiving an emotional state using a bio-parameter or bio-parameters extracted from a bio-signal detected for a short or long time.

Accordingly, to achieve the first object of the invention, there is provided an apparatus for perceiving a physical and emotional state. The apparatus includes a bio-signal detection part attached to a predetermined portion of a body for performing analog signal processing on at least one bio-signal detected from the body and outputting the processed bio-signal, and a bio-signal recognizing part for performing digital signal processing on the processed bio-signal received from the bio-signal detection part, perceiving the physical and emotional state from the result of the digital signal processing, and reporting the physical and emotional state.

To achieve the second object of the invention, there is provided a method of perceiving a physical and emotional state, including the steps of performing analog signal processing on at least one bio-signal detected from a body, and performing digital signal processing on the analog signal processed bio-signal, perceiving the physical and emotional state from the result of the digital signal processing, and reporting the physical and emotional state.

To achieve the third object of the invention, there is provided a method of perceiving an emotional state, including the steps of extracting at least one bio-parameter representing a characteristic of a body from at least one bio-signal which is detected from the body for a predetermined time, and determining the amount of variation of the extracted bio-parameter and determining a current emotional state using the determined amount of variation. The value of the bio-parameter varies with a change in the emotional state.

BRIEF DESCRIPTION OF THE DRAWINGS

The above objectives and advantages of the present invention will become more apparent by describing in detail preferred embodiments thereof with reference to the attached drawings in which:

FIG. 6 is a flowchart of a second embodiment of step 302 shown in FIG. 4 according to the present invention;

DETAILED DESCRIPTION OF THE PRESENT INVENTION

Figure 1:
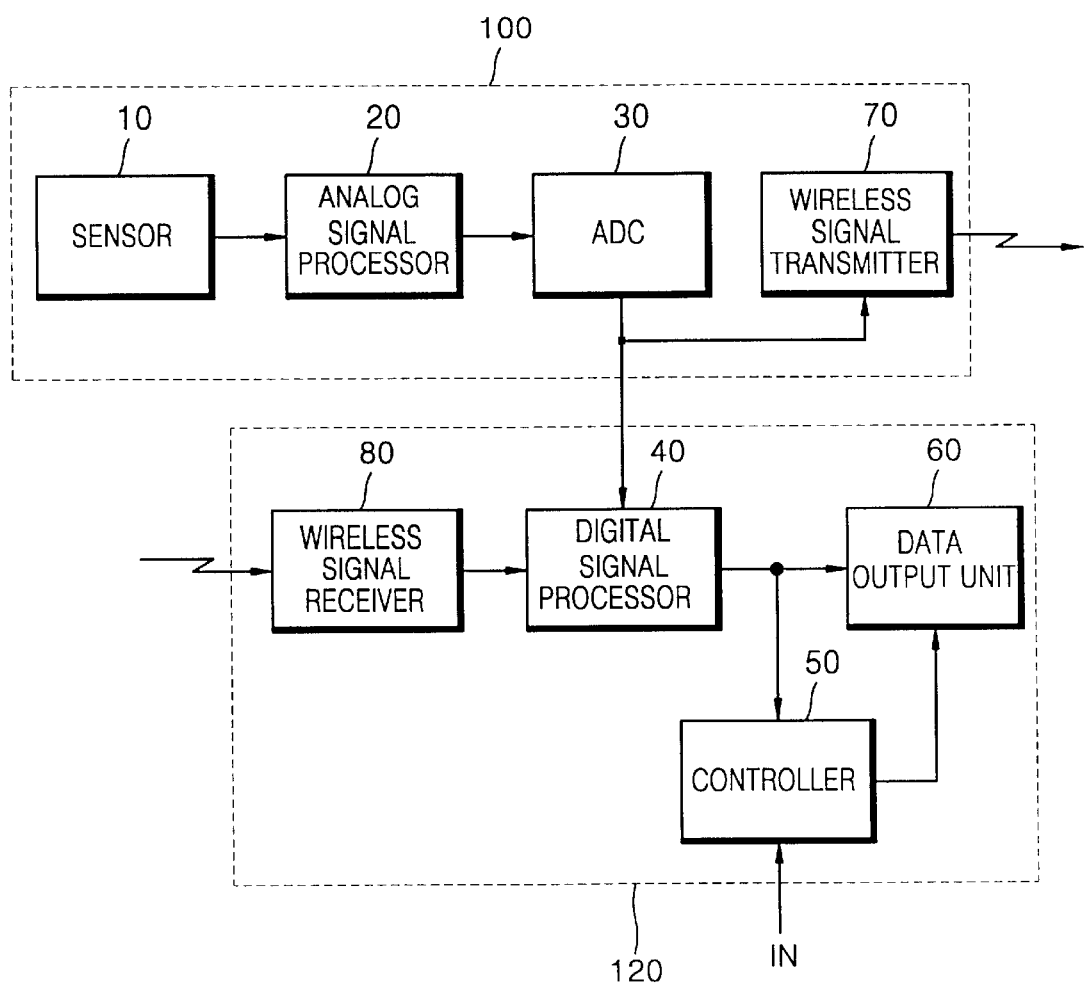
FIG. 1 is a schematic block diagram of an apparatus for perceiving a physical and emotional state according to the present invention.

Referring to FIG. 1, an apparatus for perceiving a physical and emotional state according to the present invention includes a bio-signal detection 100 and a bio-signal recognizing 120. The bio-signal detection 100 includes a sensor 10, an analog signal processor 20, an analog-to-digital converter (ADC) 30, and a wireless signal transmitter 70. The bio-signal recognizing part 120 includes a wireless signal receiver 80, a digital signal processor 40, a controller 50 and a data output unit 60.

Figure 2:
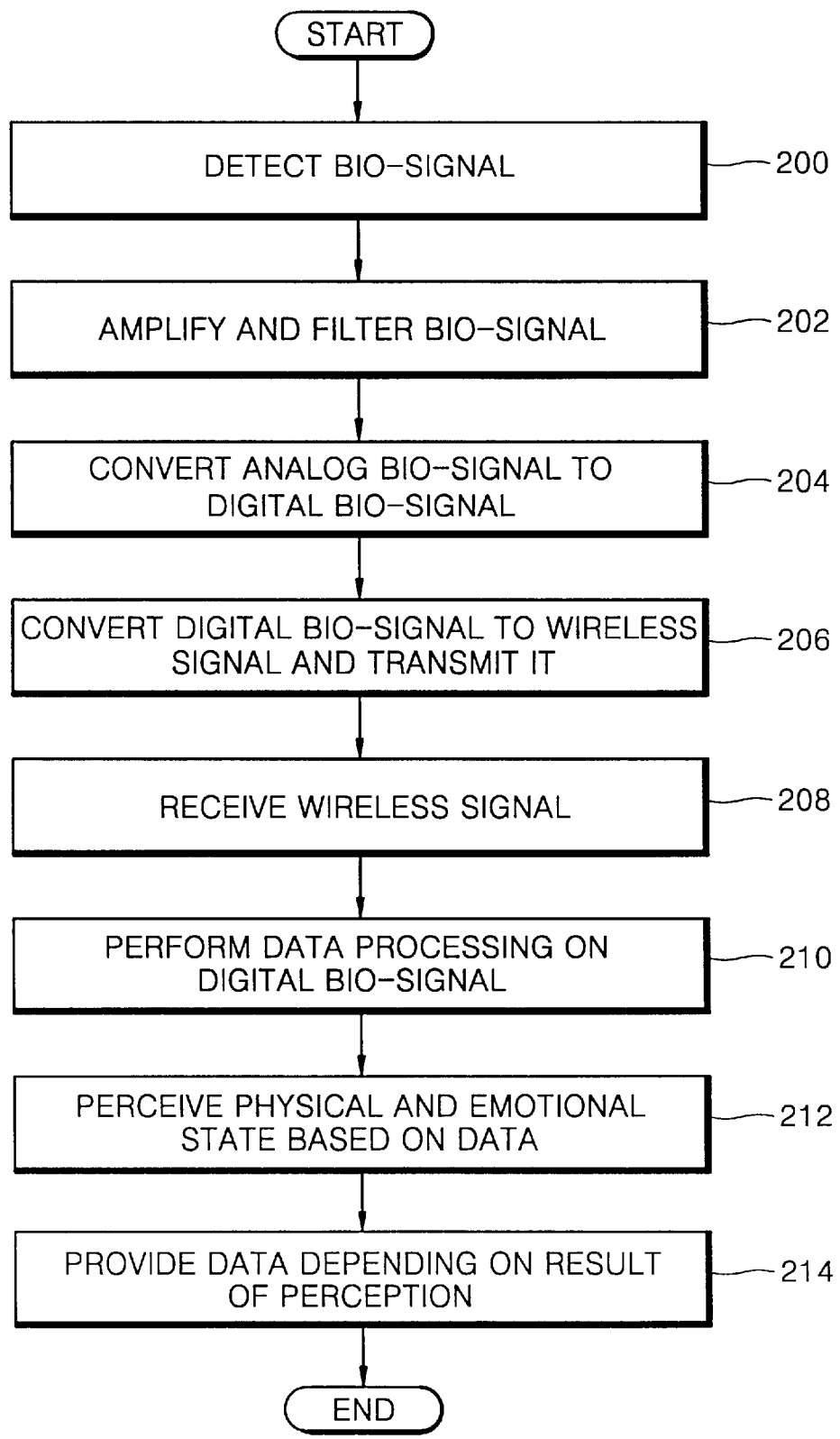
FIG. 2 is a flowchart of a method of perceiving a physical and emotional state according to the present invention, which is performed by the apparatus shown in FIG. 1.

Referring to FIG. 2, a method, performed with the apparatus shown in FIG. 1, of perceiving a physical and emotional state includes steps 200 through 206 of performing analog signal processing on a bio-signal or bio-signals detected from a human body and steps 208 through 214 of performing digital signal processing on the analog signal processed bio signal(s) and perceiving and displaying a physical and emotional state.

In the steps 200 through 206, the bio-signal detection 100 is attached to a predetermined portion of a human body, performs analog signal processing on at least one bio-signal detected from the body, and outputs the processed bio-signal to the bio-signal recognizing 120.

In the step 200, the sensor 10 in bio-signal detection 100 detects a bio-signal from a human body. For examples, the sensor 10 detects analog bio-signals corresponding to blood pressure, skin temperature, skin resistivity and so on. For this, the sensor 10 includes a blood pressure sensor (not shown) for measuring blood pressure, a skin temperature sensor (not shown) for measuring skin temperature, and a skin resistivity sensor (not shown) for measuring skin resistivity to electric current. Here, the sensor 10 may further include a respiration sensor (not shown) for measuring a respiration rate.

The blood pressure sensor may be realized as a pressure sensor such as a Piezo sensor or a strain gauge or as a Photo-electric pulse PlethysmoGraph (PPG) sensor. The blood pressure sensor is disclosed on pages 163 through 177 of a book entitled "Introduction to Biomedical Equipment Technology (2nd Edition)" written by Joseph J. Carr and John M. Brown and published by REGENTS/Prentice Hall in 1993. The Piezo sensor is disclosed on pages 167 and 168 of "Introduction to Biomedical Equipment Technology (2nd Edition)" written by Joseph J. Carr and John M. Brown, and in a book entitled "Bosch Automotive Electric-Electronic Systems Handbook" written by Robert Bosch and published by Robert Bentley in 1995. The strain gauge is disclosed on pages 113 through 122 of a book entitled "Principles of Biomedical Instrumentation and Measurement" written by Richard Aston and published by Maxwell Macmillan International Edition in 1991. The PPG sensor is disclosed on pages 207 through 209 of "Introduction to Biomedical Equipment Technology (2nd Edition)" written by Joseph J. Carr and John M. Brown.

The skin temperature sensor may be realized as a sensor which measures skin temperature using an electrode and a thermocouple. The skin temperature sensor is disclosed on pages 100 through 107 of "Principles of Biomedical Instrumentation and Measurement" written by Richard Aston. The electrode is disclosed on pages 25 through 37 of "Introduction to Biomedical Equipment Technology (2nd Edition)" written by Joseph J. Carr and John M. Brown. The thermocouple is disclosed on pages 100 through 107 of "Principles of Biomedical Instrumentation and Measurement" written by Richard Aston.

The skin resistivity sensor may be realized as a sensor which measures skin resistivity using an electrode directly or indirectly contacting skin and a comparator connected to the electrode. The skin resistivity sensor was introduced by Don C. Fowles, Robert Edelberg and David T. Lykken, in "Publication Recommendation for Electrodermal measurements", Psychophysiology published by the Society for Psychophysiological Research Inc., in 1981, pp. 232–239.

After step 200, in step 202, the analog signal processor 20 amplifies and filters the analog bio-signal detected by the sensor 10 and outputs the amplified and filtered analog bio-signal to the ADC 30. Here, a low-pass filter is usually used to eliminate high frequency noise components, but a band pass filter may be used to obtain a signal of a specific band.

In step 204, the ADC 30 converts the analog bio-signal, which has been amplified and filtered by the analog signal processor 20, to a digital bio-signal and outputs it to the wireless signal transmitter 70 or the digital signal processor 40.

In an embodiment of the present invention, the bio-signal detection 100 may communicate the digital bio-signal to the bio-signal recognizing part 120 through a wire. In this case, the digital bio-signal is transmitted to the digital signal processor 40 through a wire, and the procedure proceeds from step 204 directly to step 210.

In another embodiment of the present invention, the bio-signal detection part 100 may wirelessly communicate the digital bio-signal to the bio-signal recognizing 120. In this case, the bio-signal detection 100 may be realized as a strap-on type which may be attached to and detached from a predetermined part of a body. For example, the bio-signal detection 100 may be realized as a watch-type which can be attached to a wrist, or realized so that it can be attached to other body parts depending on the purpose of application. In addition, the bio-signal recognizing part 120 may be realized as attachable to a body and installed outside at a predetermined distance from the bio-signal detection part 100. When the wireless signal transmitter 70 transmits a digital bio-signal to the wireless signal receiver 80 over a predetermined distance, in step 206, the wireless signal transmitter 70 converts the digital bio-signal received from the ADC 30 to a wireless signal and transmits it to the bio-signal recognizing 120.

In steps 208 through 214, the bio-signal recognizing part 120 performs digital signal processing on the bio-signal processed by the bio-signal detection 100 and perceives and displays a physical and emotional state based on the result of the digital signal processing.

When the bio-signal detection 100 transmits a signal wirelessly, in step 208, the wireless signal receiver 80 in the bio-signal recognizing part 120 receives the wireless signal from the wireless signal transmitter 70 and outputs the received digital bio-signal to the digital signal processor 40. However, when the bio-signal detection part 100 transmits the digital bio-signal to the bio-signal recognizing part 120 through a wire, the procedure proceeds from step 204 directly to step 210.

In step 210, the digital signal processor 40 performs data processing on the digital bio-signal received from the ADC 30 or the wireless signal receiver 80 and outputs the result of the data processing to the controller 50 and the data output unit 60.

In step 212, the controller 50 perceives a physical and emotional state based on the data received from the digital signal processor 40 and outputs the result of the perception to the data output unit 60 as a control signal. Specifically, the controller 50 receives at least one reference value previously set through its input terminal IN and stores it. The controller 50 compares the stored reference value with the data received from the digital signal processor 40 and perceives a physical and emotional state using the result of the comparison. Here, the reference value is an average value of the bio-signals of general persons.

Figure 3:
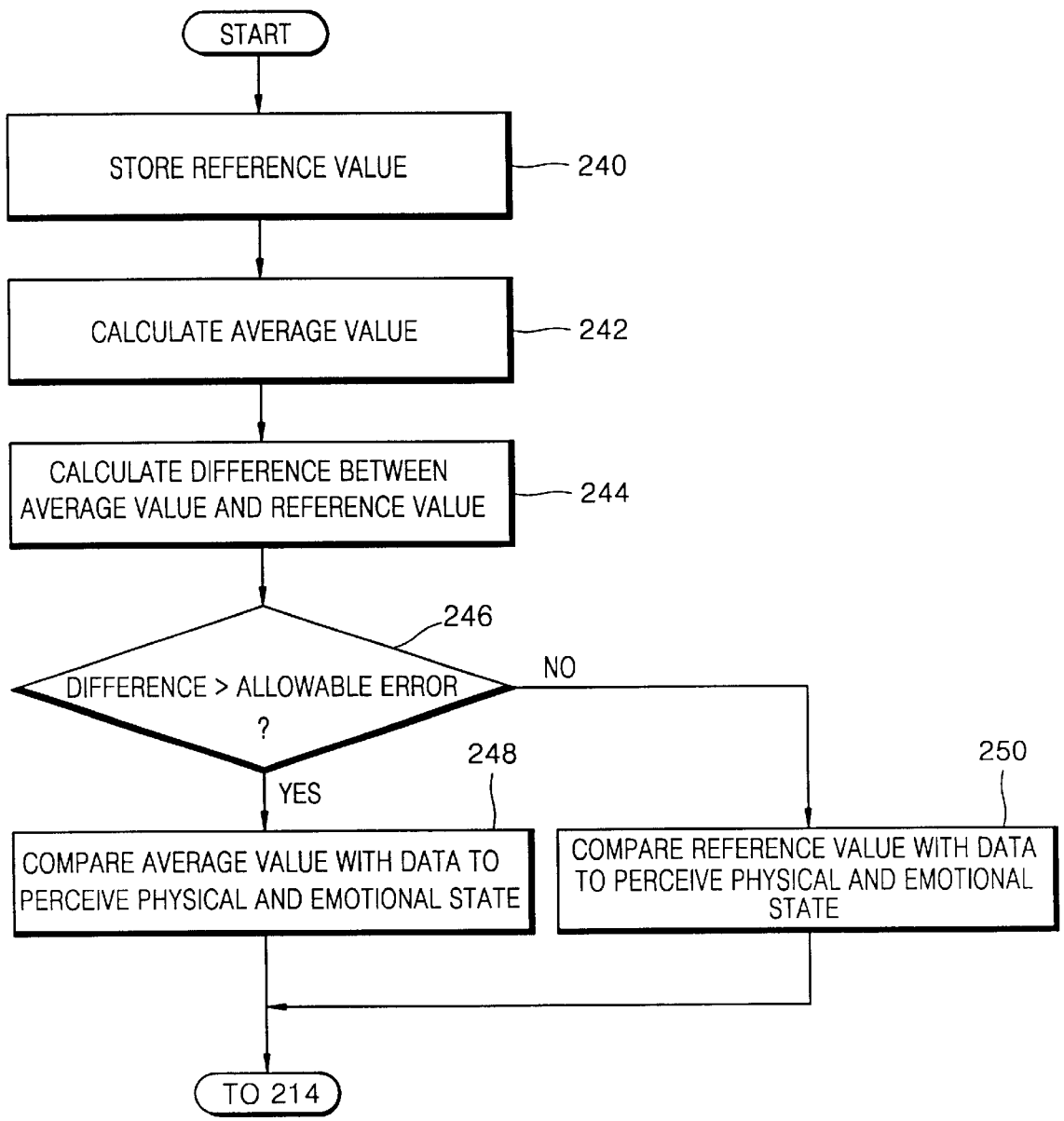
FIG. 3 is a flowchart of an embodiment of step 212 shown in FIG. 2 according to the present invention.

An embodiment of step 212 performed by the controller 50 of FIG. 2 will be described with reference to the attached drawings. Referring to FIG. 3, the embodiment of step 212 includes steps 240 through 246 of determining whether to use an average value or a reference value in perceiving a physical and emotional state, and steps 248 and 250 of perceiving the physical and emotional state using the average value or the reference value.

Referring to FIG. 3, in step 240, the controller 50 stores at least one reference value previously set. As described above, the controller 50 may receive the reference value through its input terminal IN from the outside and store it. Alternatively, the controller 50 may previously receive and store the reference value. In step 242, the average value of at least one bio-signal detected by the sensor 10 is calculated from the data output from the digital signal processor 40.

After step 242, one of the average value and the reference value is selected in response to the difference between the two values, and the selected average value or reference value is compared with the data currently output from the digital signal processor 40, thereby perceiving a physical and emotional state in steps 244 through 250. Specifically, in step 244, the difference between the average value and the reference value is calculated. Here, the average value corresponds to an average of bio-signals which the sensor 10 previously measures for a user of the apparatus of FIG. 1. In step 246, it is determined whether the difference between the average value and the reference value is greater than an allowable error. If it is determined that the difference is greater than the allowable error, in step 248, the average value is compared with the data processed in step 210 to perceive a physical and emotional state. However, if it is determined that the difference is not greater than the allowable error, in step 250, the reference value is compared with the data processed in step 210 to perceive a physical and emotional state.

To clarify the description, the operation of the controller 50 will be described below on the assumption that blood pressure, skin temperature and skin resistivity are measured by the sensor 10, as described above. The controller 50 stores predetermined first, second and third reference values of respective bio-signals corresponding to blood pressure, skin temperature and skin resistivity, respectively, and calculates and stores first, second and third average values of respective previously measured bio-signals corresponding to blood pressure, skin temperature and skin resistivity, respectively. Here, if it is determined that the difference between an X-th reference value ($1 \leq X \leq 3$) and an X-th average value is not greater than a predetermined X-th allowable error, the controller 50 compares the X-th reference value with the data received from the digital signal processor 40. If it is determined that the difference between the X-th reference value and the X-th average value is greater than the predetermined X-th allowable error, the controller 50 compares the X-th average value with the data received from the digital signal processor 40. Then, the controller 50 perceives a physical and emotional state through the result of comparison. Here, the average value instead of the reference value is used in order to exactly perceive a physical and emotional state taking into account the user's physical characteristics. For example, when blood pressure or body temperature currently measured by the sensor 10 is higher than a predetermined reference value or a calculated average value by at least a predetermined level, the controller 50 perceives excitement or anger. When skin resistivity currently measured by the sensor 10 is lower than a predetermined reference or average value by a predetermined level, the controller 50 perceives strain. This is because a person under strain sweats more than usual, and skin resistivity decreases as the person sweats more. Such physical and emotional states which can be perceived can be modified, or additional states can be added, through tests. In addition, highly reliable data can be obtained by combining perceived states. In other words, the controller 50 may perceive different physical and emotional states depending on first, second and third comparison values which are obtainable as a result of comparing the average or reference values with the data received from the digital signal processor 40, or may perceive physical and emotional states using the result of performing an OR operation or an And operation and a logical combination on the first through third comparison values. A method of perceiving an emotional state using the result of comparing the average values with the data according to the present invention will be described later.

After step 212, in step 214, the data output unit 60 provides the digital data, that is, a bio-signal and a perception signal which is received from the digital signal processor 40, to the user in the form of a voice and/or an image in response to the control signal generated by the controller 50. For this, the data output unit 60 may include a speaker and/or a monitor and may provide physical and emotional state perception data and detected bio-signal data to the user in the form of a voice and/or an image in response to the control signal of the controller 50.

Figure 4:
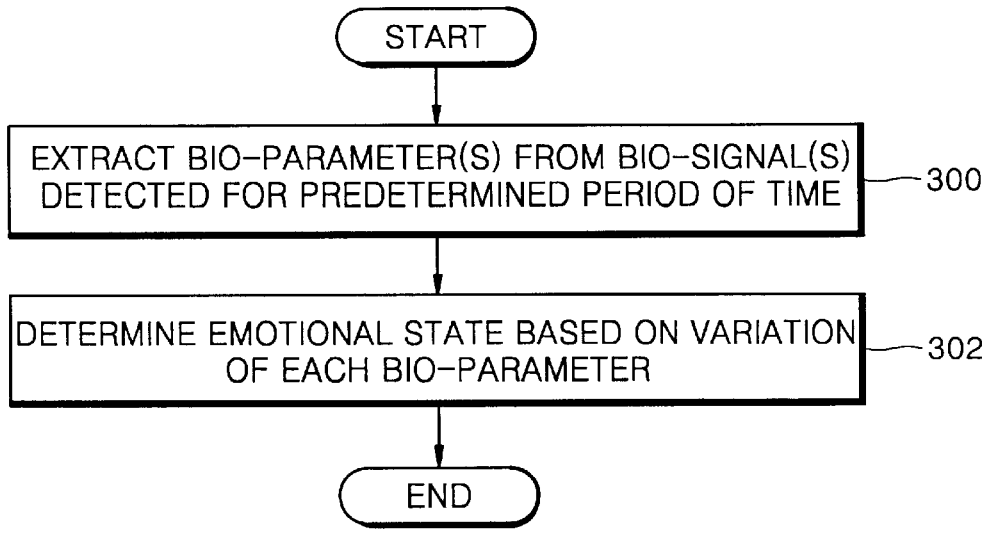
FIG. 4 is a flowchart of a method of perceiving an emotional state according to the present invention.

Hereinafter, a method of perceiving an emotional state according to the present invention and embodiments thereof will be described with reference to the attached drawings. FIG. 4 is a flowchart of a method of perceiving an emotional state according to the present invention. In steps 300 and 302, an emotional state is determined based on at least one bio-parameter extracted from at least one bio-signal detected for a predetermined period of time.

Specifically, in step 300, at least one bio-parameter representing a physical characteristic is extracted from at least one bio-signal detected from a user's body for a predetermined period of time. For example, bio-parameters representing the frequency of an electrocardiogram, the number of heartbeats and an electrocardiogram attendant upon respiration are extracted from a bio-signal having information as to blood pressure, and bio-parameters representing skin temperature and skin resistivity are extracted from bio-signals having information as to skin temperature and skin resistivity.

The value of each bio-parameter extracted in step 300 varies with a change in an emotion. The predetermined period of time may be a minimum time (referred to as a predetermined short time) taken for a changed emotion to be represented by a bio-signal, or may be a time (referred to as a predetermined long time) longer than the minimum time. For example, the predetermined short time may be 10–60 seconds, and the predetermined long time may be a time longer than 60 seconds.

In the method of perceiving an emotional state according to the present invention, bio-parameters detected for the predetermined short time and bio-parameters detected for the predetermined long time are used for perceiving a person's emotional state. In other words, bio-parameters detected for the predetermined short time are used in order to quickly perceive a rapidly changing emotional state, and bio-parameters detected for the predetermined long time are used in order to perceive an emotional state which remains for a long time.

After step 300, in step 302, the amount of variation of each bio-parameter currently extracted is determined, and a current emotional state is determined based on the determined amount of variation. Specifically, a base bio-parameter is compared with a currently extracted bio-parameter to determine the amount of variation of the currently extracted bio-parameter. Here, the base bio-parameter is a bio-parameter measured in a time for which no emotions arise, for example, for about 10 through 20 minutes for which a user's mind is calm.

The method of perceiving an emotional state shown in FIG. 4 corresponds to step 248 shown in FIG. 3 and can be performed by the controller 50. In this case, the base bio-parameter corresponds to an average value.

Embodiments of step 302 of perceiving an emotional state based on bio-parameters detected for the predetermined short time and bio-parameters detected for the predetermined long time will be described with reference to the attached drawings.

Figure 5:
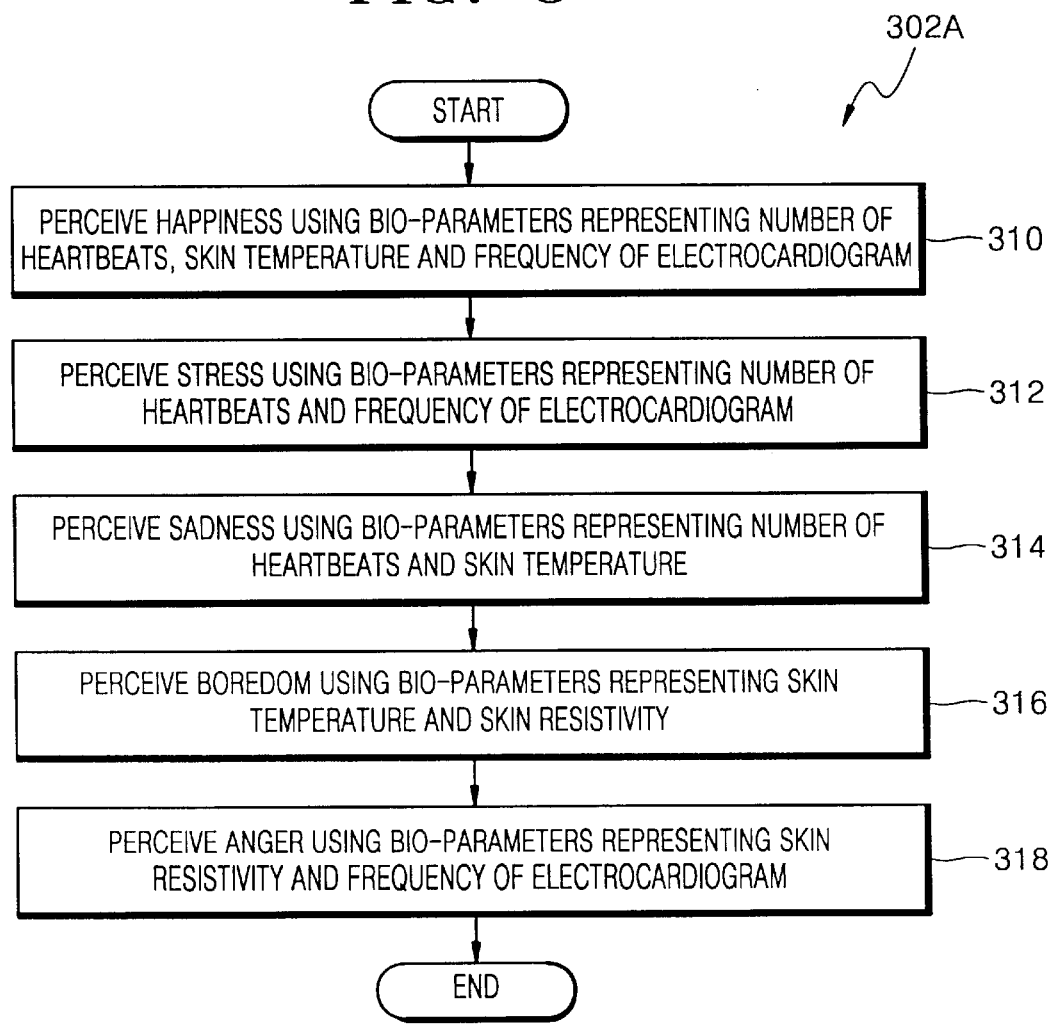
FIG. 5 is a flowchart of a first embodiment of step 302 shown in FIG. 4 according to the present invention.

FIG. 5 is a flowchart of a first embodiment 302A of step 302 shown in FIG. 4. The embodiment 302A includes steps 310 through 318 of perceiving a person's emotional state based on the amounts of variation of bio-parameters. According to the embodiment shown in FIG. 5, an emotional state is perceived using bio-parameters detected for the predetermined short time.

In step 310, happiness is perceived using bio-parameters representing the number of heartbeats, skin temperature and the frequency of an electrocardiogram. In step 312, stress is perceived using bio-parameters representing the number of heartbeats and the frequency of an electrocardiogram. In step 314, sadness is perceived using bio-parameters representing the number of heartbeats and skin temperature. In step 316, boredom is perceived using bio-parameters representing skin temperature and skin resistivity. In step 318, anger is perceived using bio-parameters representing skin resistivity and the frequency of an electrocardiogram. Steps 310 through 318 in FIG. 5 can be performed regardless of order.

FIG. 6 is a flowchart of a second embodiment 302B of step 302 shown in FIG. 4. The embodiment 302B includes steps 330 through 338 of perceiving a person's emotional state based on the amounts of variation of bio-parameters. According to the embodiment shown in FIG. 6, an emotional state is perceived using bio-parameters detected for the predetermined long time.

In step 330, boredom is perceived using bio-parameters representing skin temperature, skin resistivity, the frequency of an electrocardiogram and an electrocardiogram attendant upon respiration. In step 332, anger is perceived using bio-parameters representing skin resistivity and an electrocardiogram attendant upon respiration. In step 334, happiness is perceived using bio-parameters representing the number of heartbeats, the frequency of an electrocardiogram and a respiration rate. In step 336, sadness is perceived using bio-parameters representing the number of heartbeats and skin resistivity. In step 338, stress is perceived using bio-parameters representing skin resistivity. Here, steps 330 through 338 can be performed regardless of order.

The bio-parameters described in the embodiments 302A and 302B shown in FIGS. 5 and 6 can be determined as follows. A bio-parameter representing the frequency of an electrocardiogram may be a low frequency (LF) value obtained by integrating a power spectrum in the range of a low frequency over the result of taking the Fast Fourier Transform (FFT) of a bio-signal which contains information on blood pressure, a high frequency (HF) value obtained by integrating a power spectrum in the range of a high frequency over the result of taking FFT of a bio-signal which contains information on blood pressure, or a LF/HF obtained by dividing the LF by the HF. Here, the range of a low frequency may be 0.04–0.15 Hz, and the range of a high frequency may be 0.15–0.5 Hz.

A bio-parameter representing the number of heartbeats may be an average RR of the intervals between the positive peaks of blood pressure, or a heart rate (HR) indicating the number of heartbeats per unit time. Here, the positive peak means a usual R peak and is usually disclosed in the part related to electrocardiograms in physiological textbooks. For example, the positive peak is disclosed on pages 171 through 216 of the Korean translation of "Introduction to Biomedical Equipment Technology (2nd Edition)" written by Joseph J. Carr & John M. Brown, and which was translated into Korean by Myung-ho Lee and published by Kyungmoon in 1996. Here, the HR can be obtained in a similar way to the RR, for example, calculating the number of heartbeats for 1 minute.

A bio-parameter representing an electrocardiogram attendant upon respiration may be a respiratory sinus arrhythmia (RSA) indicating a value obtained by dividing the result of subtracting a minimum interval from a maximum interval among the intervals between positive peaks of blood pressure by the minimum interval, that is, (maximum interval-minimum interval)/minimum interval. Here, a variety of methods of extracting the RSA are widely known. For example, one of these methods is introduced by A. W. Frey, C. Hagenmiller, J Baumert, F. Grueneis, M. Dambacher, K. Theisen and M. Adt, "The Respiratory Sinus Arrhythmia as a Function of Breathing Frequency Revisited", IEEE Computer in Cardiology, pp. 41–44, 1994.

A bio-parameter representing skin temperature may be a SKin Temperature (SKT) equal to an average skin temperature. A bio-parameter representing skin resistivity may be a skin conductive level (SCL) equal to an average of reciprocals of values of skin resistivity, the number of skin conductive response (N-SCR) equal to the number of negative slope zero crossings measured from a graph expressing reciprocals of values of skin resistivity, or a skin conductive response magnitude (SCRM) equal to the sum of reciprocals of values of skin resistivity between a negative slope zero crossing and a positive slope zero crossing. Taking into account that negative or positive slope zero crossings may occur due to noise, the curve on the graph may be previously low-pass filtered.

Other bio-parameters such as a finger pulse volume (FPV) and a PPG can be extracted in step 300. Both FPV and PPG denote the amount of a blood flow. The bio-parameters, RR, HR, SKT, SCL, N-SCR, SCRM, LF, HF, LF/HF, RSA, RESP, FPV and PPG, are obtained at different times. When the embodiment 302A shown in FIG. 5 is applied, these bio-parameters are all detected for the predetermined short time. When the embodiment 302B shown in FIG. 6 is applied, these bio-parameters are all detected for the predetermined long time. These bio-parameters may be generated by the controller 50 shown in FIG. 1 as follows.

A bio-signal, which corresponds to blood pressure sensed by a blood pressure sensor (not shown) provided in the sensor 10 of FIG. 1, is processed as described before and then input to the digital signal processor 40. The controller 50 can extract bio-parameters, i.e., RR, HR, LF, HF, LF/HF, RSA and RESP, using blood pressure data generated by the digital signal processor 40. For example, the controller 50 obtains RR, RSA and HR from the blood pressure data, obtains LF and HF by performing FFT analysis on the blood pressure data, and obtains LF/HF from LF and HF. Here, instead of the bio-signal corresponding to the blood pressure sensed by the blood pressure sensor, a bio-signal corresponding to respiration sensed by a respiration sensor (not shown) may be used to obtain RESP. In this case, the bio-signal corresponding to respiration sensed by the respiration sensor provided in the sensor 10 of FIG. 1 is input to the digital signal processor 40 through the procedure described above. Then, the controller 50 extracts RESP from respiration data generated by the digital signal processor 40. A variety of methods of extracting RESP are widely known. For example, a general method of extracting RESP is introduced by Pei Z. Zhang, Walter N. Tapp, Stanley S. Reisman and Benjamin H. Natelson, "Respiration Response Curve Analysis of Heart Rate Variability", IEEE Transaction on Biomedical Engineering, Vol. 44, No. 4, pp. 321–325, April 1997.

In addition, bio-signals corresponding to skin temperature and skin resistivity, respectively, which are sensed by a skin temperature sensor (not shown) and a skin resistivity sensor (not shown), respectively, provided in the sensor 10 of FIG. 1, are processed as described before and then input to the digital signal processor 40. Then, the controller 50 can extract bio-parameters, i.e., SKT, SCL, N-SCR and SCRM, from skin temperature data and skin resistivity data generated by the digital signal processor 40.

The blood sensor provided in the sensor 10 of FIG. 1 may be realized as a PPG sensor (not shown) in order to measure FPV and PPG. The PPG sensor senses, for example, information as to a blood flow at the end of a finger. A bio-signal which contains the sensed information on blood flow is processed as described before and then input to the digital signal processor 40. Then, the controller 50 extracts FPV and PPG from blood flow data generated by the digital signal processor 40.

After extracting bio-parameters as described above, the controller 50 determines the amount of variation of each of the currently extracted bio-parameters on the basis of base bio-parameters previously extracted and determines an emotional state. In other words, step 302 shown in FIG. 4 and its embodiments 302A and 302B shown in FIGS. 5 and 6 can be performed by the controller 50.

Preferred embodiments of the embodiments 302A and 302B shown in FIGS. 5 and 6, respectively, will be described with reference to the attached drawings. Base bio-parameters are expressed like RR(base), HR(base), SKT (base), SCL(base), N-SCR(base), SCRM(base), LF(base), HF(base), LF/HF(base), RSA(base) and RESP(base).

Figure 7A:
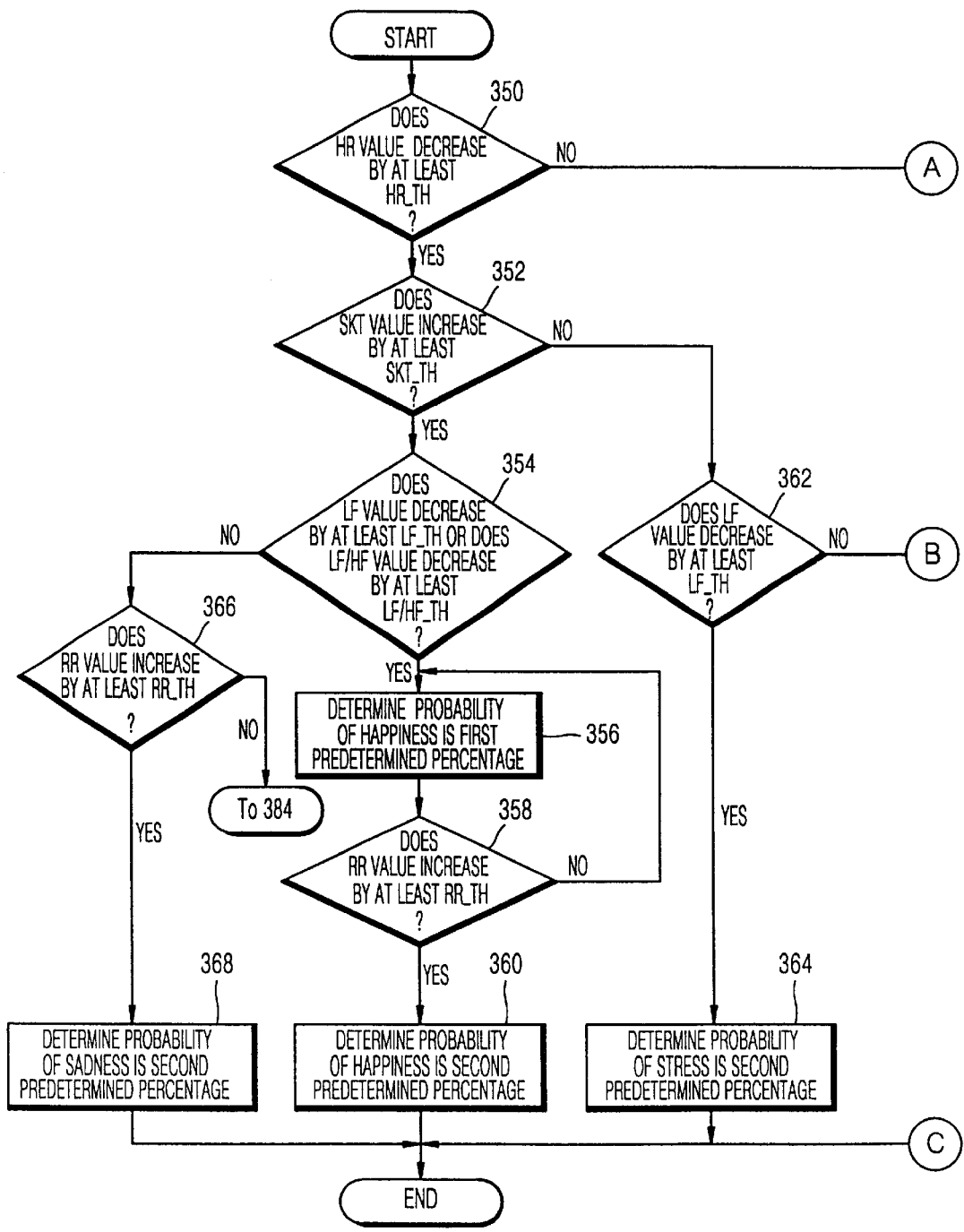
FIG. 7 (comprises of FIGS. 7A and 7B) is a flowchart of a preferred embodiment of the embodiment shown in FIG. 5 according to the present invention.
Figure 7B:
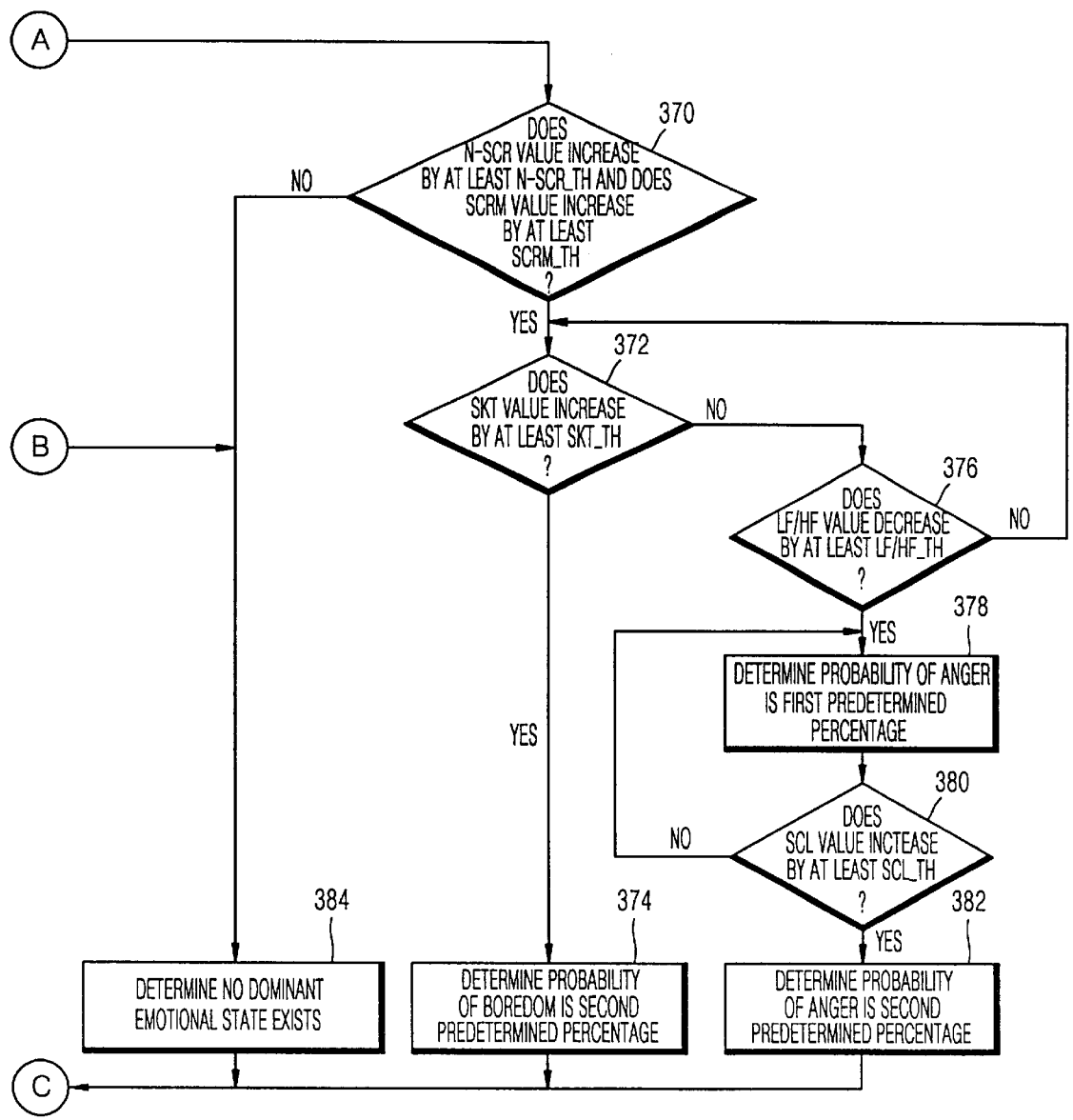

FIG. 7 (comprised of FIGS. 7A and 7B) is flowchart of a preferred embodiment of the embodiment 302A shown in FIG. 5 and includes steps 350 through 360 of determining happiness, steps 362 and 364 of determining stress, steps 366 and 368 of determining sadness, steps 370 through 374 of determining boredom, steps 376 through 382 of determining anger, and a step 384 of determining that a specific emotional state does not exist. In the embodiment shown in FIG. 7, bio-parameters, RR, HR, SKT, SCL, N-SCR, SCRM, LF and LF/HF, which are detected for the predetermined short time, are used to determine an emotional state.

In steps 350 through 360, it is determined whether an emotional state is happiness in an initial state. The initial state denotes a state in which any emotion is not dominant, for example, a state in which emotions (or mental states) such as happiness, sadness, stress, anger and boredom are uniform or mixed.

After step 300, in step 350 it is determined whether a HR value decreases by at least a HR threshold value (referred to as HR_th) in the initial state. More specifically, it is determined whether a value, which is obtained by subtracting the HR_th from the HR(base), is greater than the HR value. If it is determined that the HR value decreases by at least the HR_th, in step 352 it is determined whether a SKT value increases by at least a SKT threshold value (referred to as SKT_th). When the HR value decreases by at least the HR_th, probability that the emotional state is happiness, sadness or stress is, for example, 50%. However, since it is still difficult to determine which one among happiness, sadness and stress is the emotional state, it is determined whether the SKT value increases by at least the SKT_th. More specifically, it is determined whether a value obtained by summing the SKT(base) and the SKT_th is less than the SKT value.

If it is determined that the SKT value increases by at least the SKT_th, in step 354 it is determined whether a LF value decreases by at least a LF threshold value (referred to as LF_th) or whether a LF/HF value decreases by at least a LF/HF threshold value (referred to as LF/HF_th). When the SKT value increases by at least the SKT_th, probability that the emotional state is happiness or sadness is, for example, 60%. However, since it is still difficult to determine which one of happiness and sadness is the emotional state, it is determined whether the LF value decreases by at least the LF_th or whether the LF/HF value decreases by at least the LF/HF_th. More specifically, it is determined whether a value obtained by subtracting the LF_th from the LF(base) is greater than the LF value, or whether a value obtained by subtracting the LF/HF_th from the LF/HF(base) is greater than the LF/HF value.

If it is determined that the LF value decreases by at least the LF_th or that the LF/HF value decreases by at least the LF/HF_th, in step 356 it is determined that probability that the emotional state is happiness is a first predetermined percentage. Here, the first predetermined percentage may be set at 70%. Thereafter, in step 358, it is determined whether a RR value increases by at least a RR threshold value (referred to as RR_th). More specifically, it is determined whether a value obtained by summing the RR(base) and the RR_th is less than the RR value. If it is determined that the RR value does not increase by at least the RR_th, the procedure goes back to step 356. However, if it is determined that the RR value increases by at least the RR_th, in step 360 it is determined that probability that the emotional state is happiness is a second predetermined percentage greater than the first predetermined percentage. Here, the second predetermined percentage may be set at 80%.

In steps 362 and 364, it is determined whether the emotional state is stress as follows. If it is determined that the SKT value does not increase by at least the SKT_th in step 352, it is determined whether the LF value decreases by at least the LF_th in step 362. When the SKT value does not increase by at least the SKT_th, probability that the emotional state is stress is still, for example, 50%. Accordingly, it is still difficult to determine that the emotional state is stress. Therefore, it is determined whether the LF value decreases by at least the LF_th. More specifically, it is determined whether a value obtained by subtracting the LF_th from the LF(base) is greater than the LF value. If it is determined that the LF value decreases by at least the LF_th, in step 364 it is determined that probability that the emotional state is stress is the second predetermined percentage.

Thereafter, in steps 366 and 368, it is determined whether the emotional state is sadness as follows. If it is determined that the LF value does not decrease by at least the LF_th and that the LF/HF value does not decrease by at least the LF/HF_th in step 354, it is determined whether the RR value increases by at least the RR_th in step 366. When the LF value does not decrease by at least the LF_th and the LF/HF value does not decrease by at least the LF/HF_th, probability that the emotional state is sadness is still, for example, 60%. Since it is still difficult to determine that the emotional state is really sadness, it is determined whether the RR value increases by at least the RR_th. More specifically, it is determined whether a value obtained by summing the RR(base) and the RR_th is less than the RR value. If it is determined that the RR value increases by at least the RR_th, in step 368 it is determined that probability that the emotional state is sadness is the second predetermined percentage.

Next, in steps 370 through 374, it is determined whether the emotional state is boredom. If it is determined that the HR value does not decrease by at least the HR_th in step 350, in step 370 it is determined whether a N-SCR value increases by at least a N-SCR threshold value (referred to as N-SCR_th) and whether a SCRM value increases by at least a SCRM threshold value (referred to as SCRM_th). When the HR value does not decrease by at least the HR_th, the emotional state is still the initial state. Therefore, step 370 is performed. More specifically, it is determined whether a value obtained by summing the N-SCR(base) and the N-SCR_th is less than the N-SCR value, and whether a value obtained by summing the SCRM(base) and the SCRM_th is less than the SCRM.

If it is determined that the N-SCR value increases by at least the N-SCR_th and that the SCRM value increases by at least the SCRM_th, in step 372 it is determined whether the SKT value increases by at least the SKT_th. When the N-SCR value increases by at least the N-SCR_th and the SCRM value increases by at least the SCRM_th, probability that the emotional state is anger or boredom is, for example, 50%. Accordingly, it is difficult to determine that the emotional state is anger or that it is boredom. Therefore, it is determined whether the SKT value increases by at least the SKT_th. More specifically, it is determined whether the sum of the SKT(base) and the SKT_th is less than the SKT value. If it is determined that the SKT value increases by at least the SKT_th, in step 374 it is determined that probability that the emotional state is boredom is the second predetermined percentage.

In step 376 through 382, it is determined whether the emotional state is anger. If it is determined that the SKT value does not increase by at least the SKT_th in step 372, it is determined whether the LF/HF value decreases by at least the LF/HF_th in step 376. When the SKT value does not increase by at least the SKT_th, probability that the emotional state is anger is still, for example, 50%. Accordingly, it is still uncertain that the emotional state is anger. Therefore, it is determined whether the LF/HF value decreases by at least the LF/HF_th. More specifically, it is determined whether a value obtained by subtracting the LF/HF_th from the LF/HF(base) is greater than the LF/HF value.

If it is determined that the LF/HF value does not decrease by at least the LF/HF_th, the procedure goes back to step 372. However, it is determined that the LF/HF value decreases by at least the LF/HF_th, in step 378 it is determined that probability that the emotional state is anger is the first predetermined percentage. Thereafter, in step 380, it is determined whether a SCL value increases by at least a SCL threshold value (referred to as SCL_th). If it is determined that the SCL value does not increase by at least the SCL_th, the procedure goes back to step 378. However, if it is determined that the SCL value increases by at least the SCL_th, in step 382 it is determined that probability that the emotional state is anger is the second predetermined percentage.

In the embodiment shown in FIG. 7, if it is determined that the LF value does not decrease by at least the LF_th in step 362, if it is determined that the N-SCR value does not increase by at least the N-SCR_th or that the SCRM value does not increase be at least the SCRM_th in step 370, or if it is determined that the RR value does not increase by at least the RR_th in step 366, it may be determined that no dominant emotional state exists in step 384. In other words, it is determined that it is difficult to determine a particular emotional state.

Figure 8B:
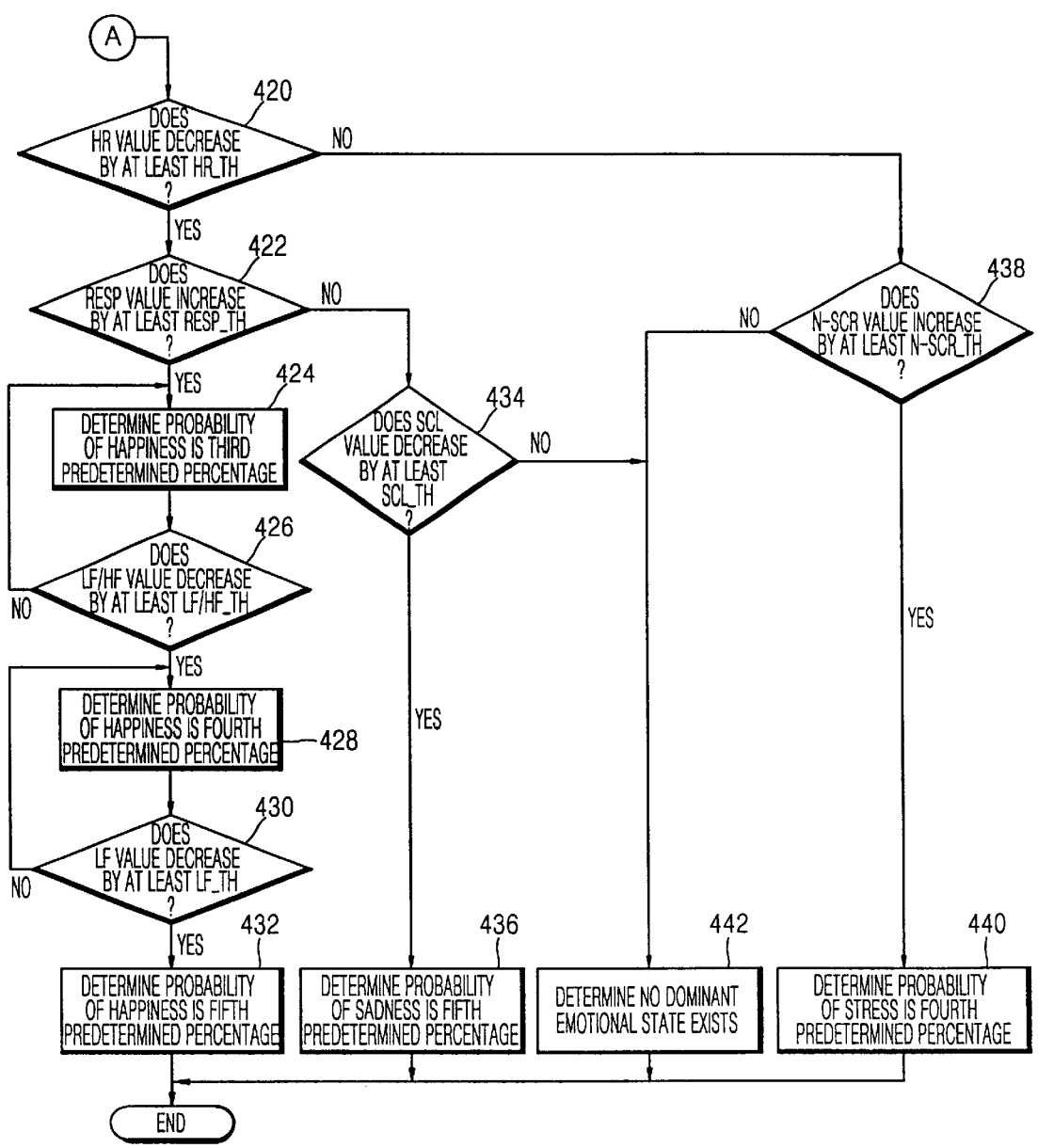
FIG. 8 (comprises of FIGS. 8A and 8B) is a flowchart of a preferred embodiment of the embodiment shown in FIG. 6 according to the present invention.

FIG. 8 (comprised of FIGS. 8A and 8B) is a flowchart of a preferred embodiment of the embodiment 302B shown in FIG. 6 and includes steps 400 through 414 of determining boredom, steps 416 and 418 of determining anger, steps 420 through 432 of determining happiness, steps 434 and 436 of determining sadness, steps 438 and 440 of determining stress, and step 442 of determining that a specific emotional state does not exist. In the embodiment shown in FIG. 8, bio-parameters, HR, SKT, SCL, N-SCR, SCRM, LF, HF, LF/HF, RSA and RESP which are detected for the predetermined long time, are used to determine an emotional state.

In steps 400 through 414, it is determined whether an emotional state is boredom in an initial state as follows. In step 400, it is determined whether a RSA value decreases by at least a RSA threshold value (referred to as RSA_th), whether a SCL value increases by at least a SCL_th, and whether a SCRM value increases by at least a SCRM_th. More specifically, it is determined whether a value obtained by subtracting the RSA_th from the RSA(base) is greater than the RSA value, whether the sum of the SCL(base) and the SCL_th is less than the SCL value, and whether the sum of the SCRM(base) and the SCRM_th is less than the SCRM value. If it is determined that the RSA value decreases by at least the RSA_th, that the SCL value increases by at least the SCL_th, and that the SCRM value increases by at least the SCRM_th, it is determined whether a N-SCR value increases by at least a N-SCR_th in step 402. More specifically, it is determined whether the sum of the N-SCR(base) and the N-SCR_th is less than the N-SCR value. If it is determined that the N-SCR value increases by at least the N-SCR_th, in step 404 it is determined whether a SKT value increases by at least a SKT_th. More specifically, it is determined whether the sum of the SKT (base) and the SKT_th is less than the SKT value. If it is determined that the SKT value increases by at least the SKT_th, in step 406 it is determined that probability that the emotional state is boredom is a third predetermined percentage. Here, the third predetermined percentage may be set at 60%.

After step 406, it is determined whether a HF value decreases by at least a HF threshold value (referred to as HF_th) in step 408. More specifically, it is determined whether a value obtained by subtracting the HF_th from the HF(base) is greater than the HF value. If it is determined that the HF value does not decrease by at least the HF_th, the procedure goes back to step 406. However, if it is determined that the HF value decreases by at least the HF_th, in step 410, it is determined that probability that the emotional state is boredom is a fourth predetermined percentage greater than the third predetermined percentage. Here, the fourth predetermined percentage may be set at 70%.

After step 410, it is determined whether a LF value decreases by at least a LF_th in step 412. More specifically, it is determined whether a value obtained by subtracting the LF_th from the LF(base) is greater than the LF value. If it is determined that the LF value does not decrease by at least the LF_th, the procedure goes back to step 410. However, if it is determined that the LF value decreases by at least the LF_th, in step 414 it is determined that probability that the emotional state is boredom is a fifth predetermined percentage greater than the fourth predetermined percentage. Here, the fifth predetermined percentage may be set at 80%.

Next, in steps 416 and 418, it is determined whether the emotional state is anger. If it is determined that the N-SCR value does not increase by at least the N-SCR_th in step 402, it is determined that probability that the emotional state is anger is the fifth predetermined percentage in step 416. If it is determined that the SKT does not increase by at least the SKT_th in step 404, it is determined that probability that the emotional state is anger is the third predetermined percentage in step 418.

Next, in steps 420 through 432, it is determined whether the emotional state is happiness. If it is determined that the RSA value does not decrease by at least the RSA_th, that the SCL value does not increase by at least the SCL_th, or that the SCRM value does not increase by at least the SCRM_th in step 400, it is determined whether a HR value decreases by at least a HR_th in step 420. More specifically, it is determined whether a value obtained by subtracting the HR_th from the HR (base) is greater than the HR value. If it is determined that the HR value decreases by at least the HR_th, in step 422 it is determined whether a RESP value increases by at least a RESP threshold value (referred to as RESP_th). More specifically, it is determined whether the sum of the RESP (base) and the RESP_th is less than the RESP value. If it is determined that the RESP value increases by at least the RESP_th, in step 424 it is determined that probability that the emotional state is happiness is the third predetermined percentage.

After step 424, it is determined whether a LF/HF value decreases by at least a LF/HF_th in step 426. More specifically, it is determined whether a value obtained by subtracting the LF/HF_th from the LF/HF (base) is greater than the LF/HF value. If it is determined that the LF/HF value does not decrease by at least the LF/HF_th, the procedure goes back to step 424. However, if it is determined that the LF/HF value decreases by at least the LF/HF_th, in the step 428, it is determined that probability that the emotional state is happiness is the fourth predetermined percentage.

After step 428, it is determined whether the LF value decreases by at least the LF_th in step 430. More specifically, it is determined whether a value obtained by subtracting the LF_th from the LF(base) is greater than the LF value. If it is determined that the LF value does not decrease by at least the LF_th, the procedure goes back to step 428. However, if it is determined that the LF value decreases by at least the LF_th, in step 432 it is determined that probability that the emotional state is happiness is the fifth predetermined percentage.

Next, in steps 434 and 436, it is determined whether the emotional state is sadness. If it is determined that the RESP value does not increase by at least the RESP_th in step 422, it is determined whether the SCL value decreases by at least the SCL_th in step 434. More specifically, it is determined whether a value obtained by subtracting the SCL_th from the SCL(base) is greater than the SCL value. If it is determined that the SCL value decreases by at least the SCL_th, in step 436 it is determined that probability that the emotional state is sadness is the fifth predetermined percentage.

Next, in steps 438 and 440, it is determined whether the emotional state is stress. If it is determined that the HR value does not decrease by at least the HR_th in step 420, it is determined whether the N-SCR value increases at least the N-SCR_th in step 438. More specifically, it is determined whether the sum of the N-SCR (base) and the N-SCR_th is less than the N-SCR value. If it is determined that the N-SCR value increases by at least the N-SCR_th, in step 440 it is determined that probability that the emotional state is stress is the fourth predetermined percentage.

In the embodiment shown in FIG. 8, if it is determined that the SCL value does not decrease by at least the SCL_th in step 434, or if it is determined that the N-SCR value does not increase by at least the N-SCR_th in step 438, it may be determined that no dominant emotional state exists in step 442.

In the embodiments shown in FIGS. 7 and 8, when probability that at least one emotional state exists is a Y-th predetermined percentage ($1 \leq Y \leq 5$), probability that each of the remaining emotional states exists is obtained by dividing the result of subtracting the Y-th predetermined percentage from 100% by the number of the remaining emotional states. For example, when probability that the emotional state is anger is 70%, probability that the current emotional state is happiness, sadness, boredom or stress is 7.5% for each of these remaining emotional states.

According to an embodiment of the present invention, over 20 children were examined to measure the reaction of an Autonomous Nervous System (ANS) in each of the five emotional states, i.e., anger, boredom, happiness, sadness and stress, regardless of sex, using bio-parameters, i.e., HR, RESP, FPV, SKT, SCL, N-SCR, SCRM, HF, LF, LF/HF and RR, detected for the predetermined short time. The results of measuring the reaction are shown in Table 1 below.

TABLE 1

|  | HR | RESP | FPV | SKT | SCL | N-SCR | SCRM | HF | LF | LF/HF | RR |
|---|---|---|---|---|---|---|---|---|---|---|---|
| Anger |  |  | ↓? | ↑ | ↑ | ↑ |  |  | ↓ |  |  |
| Boredom |  |  |  | ↑ | ↑ | ↑ |  | ↓? |  |  |  |
| Happiness | ↓ | ↑? |  | ↑ |  |  |  |  | ↓ | ↓ | ↑ |
| Sadness | ↓ |  | ↑? | ↑ |  |  |  |  |  |  | ↑ |
| Stress | ↓ |  |  |  |  | ↑? |  |  |  | ↓ |  |

Here, ↑ denotes that the value of a detected bio-parameter increased over the value of a base bio-parameter, ↓ denotes that the value of a detected bio-parameter decreased below the value of a base bio-parameter, and ? denotes that the value of a detected bio-parameter did not acutely increase over or decrease below the value of a base bio-parameter. A blank cell in Table 1 denotes that a slight amount of variation occurred. Accordingly, bio-parameters which did not change significantly or changed only slightly were not used when an emotional state was determined according to the embodiment shown in FIG. 7.

According to another embodiment of the present invention, over 20 children were examined to measure the reaction of an ANS in each of the five emotional states, i.e., anger, boredom, happiness, sadness and stress, regardless of sex, using bio-parameters, i.e., HR, RESP, RSA, PPG, SKT, SCL, N-SCR, SCRM, HF, LF and LF/HF, detected for the predetermined short time. The results of measuring the reaction are shown in Table 2 below.

TABLE 2

|  | HR | RESP | RSA | PPG | SKT | SCL | N-SCR | SCRM | HF | LF | LF/HF |
|---|---|---|---|---|---|---|---|---|---|---|---|
| Anger |  |  | L | L? |  | H | H | H |  |  |  |
| Boredom |  |  | L |  | H | H |  | H | L | L |  |
| Happiness | L | H |  | H? |  |  |  |  |  | L | L |
| Sadness | L |  |  | L? | L |  |  |  |  |  |  |
| Stress |  |  |  |  |  |  | H |  |  |  |  |

Here, H denotes that the value of a detected bio-parameter was greater than the value of a base bio-parameter, L denotes that the value of a detected bio-parameter was less than the value of a base bio-parameter, and ? denotes that the value of a detected bio-parameter did not significantly greater or less (depending on whether H? or L? appears in the table) than the value of a base bio-parameter. A blank cell in Table 2 denotes that a slight amount of variation occurred. Accordingly, bio-parameters which did not change significantly or changed only slightly were not used when an emotional state was determined according to the embodiment shown in FIG. 8.

As seen from Tables 1 and 2, some bio-parameters undergo particular change while others do not, in each of the emotional states. Therefore, a method of perceiving an emotional state according to the present invention can determine an emotional state using a particular change in a bio-parameter, as described above.

In this specification, emotional states which can be perceived are limited to five kinds, i.e., anger, boredom, happiness, sadness and stress. However, an apparatus and method of perceiving an emotional state according to the present invention are not restricted to these five emotional states and can perceive a variety of emotional states using bio-parameters, i.e., HR, RESP, RSA, PPG, SKT, SCL, N-SCR, SCRM, HF, LF, LF/HF, FPV and RR.

As described above, according to an apparatus and method for perceiving a physical and emotional state according to the present invention, the apparatus can be conveniently attached to a predetermined portion of a user's body, a bio-signal transmitted wirelessly or through a wire can be easily detected, a physical and emotional state which is perceived based on the detected bio-signal can be reported to the user, and a rapidly changing emotional state or an emotional state which remains for a long time can be perceived in real time.

What is claimed is:

1. An apparatus for perceiving a physical and emotional state, comprising:
   a bio-signal detection part for attaching to a predetermined portion of a user's body, and for performing analog signal processing on at least one bio-signal detected from the body and outputting the processed bio-signal; and
   a bio-signal recognizing part for performing digital signal processing on each processed bio-signal received from the bio-signal detection part, perceiving the physical and emotional state of the user from the result of the digital signal processing, and
   reporting the physical and emotional state to the user.

2. The apparatus of claim 1, wherein the bio-signal detection part comprises:
   a sensor for detecting the bio-signal from the body in analog form;
   an analog signal processor for amplifying and filtering the analog bio-signal detected by the sensor; and
   an analog-to-digital converter for converting the amplified and filtered analog bio-signal into a digital bio-signal, and
   the bio-signal recognizing part comprises:
   a digital signal processor for performing data processing on the digital bio-signal;
   a controller for perceiving the physical and emotional state from data processed by the digital signal processor and outputting the perceived result as a control signal; and
   a data output unit for outputting the data processed by the digital signal processor in predetermined form in response to the control signal.

3. The apparatus of claim 2, wherein the sensor comprises:
   a blood pressure sensor for measuring blood pressure;
   a skin temperature sensor for measuring skin temperature; and
   a skin resistivity sensor for measuring skin resistivity.

4. The apparatus of claim 3, wherein the blood sensor is a Piezo sensor or a strain gauge pressure sensor.

5. The apparatus of claim 3, wherein the skin temperature sensor measures skin temperature using an electrode and a thermocouple.

6. The apparatus of claim 3, wherein the skin resistivity sensor measures skin resistivity using an electrode and a comparator.

7. The apparatus of claim 2, wherein the bio-signal detection part further comprises a wireless signal transmitter for converting the digital bio-signal output from the analog-to-digital converter into a wireless signal and transmitting the wireless signal, and the bio-signal recognizing part further comprises a wireless signal receiver for receiving the wireless signal and outputting it to the digital signal processor as the digital bio-signal.

8. The apparatus of claim 2, wherein the controller stores at least one reference value, compares the stored reference value with the data processed by the digital signal processor, and perceives the physical and emotional state from the result of the comparison.

9. The apparatus of claim 8, wherein the controller calculates an average value of at least one bio-signal detected by the sensor from data previously processed by the digital signal processor, selects one of the average value and the reference value in response to the difference between the average value and the stored reference value, and compares the selected average value or the selected reference value with the data currently processed by the digital signal processor, to perceive the physical and emotional state.

10. The apparatus of claim 1, wherein the bio-signal detection means is a strap-on type for removably attaching to a predetermined portion of a body.

11. The apparatus of claim 1, wherein the bio-signal recognizing part comprises logic circuitry for perceiving at least one emotional state when at least two comparison values exceed a respective predetermined threshold value associated with a comparison, wherein each comparison value is based on a sum of, or a difference between, one of the digitally processed bio-signals and a respective reference value or a respective average value of the bio-signal.

12. The apparatus of claim 11, wherein the reported emotional state comprises an indication representing the probability of the perceived emotional state.

13. A method of perceiving a physical and emotional state, comprising the steps of:
   (a) performing analog signal processing on at least one bio-signal detected from a user's body; and
   (b) performing digital signal processing on the analog signal processed bio-signal, perceiving the physical and emotional state of the user from the result of the digital signal processing, and reporting the physical and emotional state to the user.

14. The method of claim 13, wherein step (a) comprises the steps of:
   (a1) detecting the bio-signal from the body;
   (a2) amplifying and filtering the detected analog bio-signal; and
   (a3) converting the amplified and filtered analog bio-signal into a digital bio-signal, and
   step (b) comprises the steps of:
   (b1) performing data processing on the digital bio-signal;
   (b2) perceiving the physical and emotional state from the resultant data of the data processing of step (b1); and
   (b3) providing the data to the user in response to the perceived result.

15. The method of claim 14, wherein step (a) further comprises the step of converting the digital bio-signal into a wireless signal and transmitting the wireless signal after step (a3), and step (b) further comprises the step of receiving the wireless signal before step (b1).

16. The method of claim 14, wherein step (b2) comprises the steps of:
   storing at least one reference value; and
   comparing the stored reference value with the resultant data of step (b1) and perceiving the physical and emotional state based on the result of the comparison.

17. The method of claim 14, wherein step (b2) comprises the steps of:
   storing at least one reference value;
   calculating an average value of least one bio-signal detected in the step (a1) from data which is previously processed in the step (b1);
   obtaining the difference between the average value and the reference value;
   determining whether the difference is greater than a predetermined allowable error;
   comparing the average value with the resultant data of step (b1) and perceiving the physical and emotional state from the result of the comparison, when it is determined that the difference is greater than the predetermined allowable error; and
   comparing the reference value with the resultant data of step (b1) and perceiving the physical and emotional state from the result of the comparison, when it is determined that the difference is not greater than the predetermined allowable error.

18. The method of claim 13, wherein perceiving the emotional state in step (b) comprises:
   calculating an average value of at least one of the digitally processed bio-signals detected from a body;
   determining whether a difference between the average value and a reference value associated with the digitally processed bio-signal exceeds a predetermined threshold value;
   perceiving the emotional state based on a comparison of the average value and the digitally processed bio-signal when the threshold is exceeded; and
   perceiving the emotional state based on a comparison of the reference value and the digitally processed bio-signal when the threshold value is not exceeded.

19. The method of claim 18, wherein the perceived emotional state is based on at least two digitally processed bio-signals.

20. The method of claim 19, wherein perceiving the emotional state further comprises determining whether a result of each of the comparisons of each of the at least two digitally processed bio-signals with the respective associated reference or average value exceeds a second predetermined threshold value respectively associated with each bio-signal.

21. The method of claim 19, wherein the reporting the emotional state comprises providing an indication representing the probability of the perceived emotional state.

22. A method of perceiving an emotional state, comprising the steps of:
   (c) extracting at least one bio-parameter representing a characteristic of a body from at least one bio-signal which is detected from the body of a user for a predetermined time; and
   (d) determining an amount of variation of the extracted bio-parameter;
   (e) determining a current emotional state using the determined amount of variation, wherein the value of the bio-parameter varies with a change in the emotional state; and
   (f) reporting the determined emotional state to the user.

23. The method of claim 22, wherein in step (c), bio-parameters representing the frequency of an electrocardiogram, number of heartbeats and an electrocardiogram attendant upon respiration are extracted from a bio-signal having information as to blood pressure, and bio-parameters representing skin temperature and skin resistivity are extracted from a bio-signal having information as to skin temperature and a bio-signal having information as to skin resistivity.

24. The method of claim 23, wherein step (d) comprises the steps of:

(d11) perceiving happiness using the bio-parameters representing the number of heartbeats, the skin temperature and the frequency of an electrocardiogram;

(d12) perceiving stress using the bio-parameters representing the number of heartbeats and the frequency of an electrocardiogram;

(d13) perceiving sadness using the bio-parameters representing the number of heartbeats and the skin temperature;

(d14) perceiving boredom using the bio-parameters representing the skin temperature and the skin resistivity; and (d15) perceiving anger using the bio-parameters representing the skin resistivity and the frequency of an electrocardiogram, and the predetermined time is a minimum time taken for a changed emotion to be represented by a bio-signal when there is a change in the emotion.

25. The method of claim 23, wherein the step (d) comprises the steps of:

(d21) perceiving boredom using the bio-parameters representing the skin temperature, the skin resistivity, the frequency of an electrocardiogram and the electrocardiogram attendant upon respiration;

(d22) perceiving anger using the bio-parameters representing the skin resistivity and the electrocardiogram attendant upon respiration;

(d23) perceiving happiness using the bio-parameters representing the number of heartbeats, the frequency of an electrocardiogram and a rate of the respiration;

(d24) perceiving sadness using the bio-parameters representing the number of heartbeats and the skin resistivity; and (d25) perceiving stress using the bio-parameters representing the skin resistivity, and the predetermined time is longer than a minimum time taken for a changed emotion to be represented by a bio-signal when there is a change in the emotion, and the rate of the respiration is extracted from the bio-signal having information as to the blood pressure in step (c).

26. The method of claim 23, the bio-parameters representing the frequency of an electrocardiogram are a low frequency (LF) indicating a value obtained by integrating a power spectrum in a low frequency range over the Fast Fourier Transform (FFT) of the bio-signal having the information as to the blood pressure, a high frequency (HF) indicating a value obtained by integrating a power spectrum in a high frequency range over the FFT of the bio-signal having the information as to the blood pressure, and a LF/HF indicating a value obtained by dividing the LF by the HF; the bio-parameters representing the number of heartbeats are a RR indicating an average value of the intervals between the positive peaks of the blood pressure and a heart rate (HR) indicating the number of heartbeats for a unit time period; the bio-parameter representing the electrocardiogram attendant upon respiration is a respiratory sinus arrhythmia (RSA) indicating a value obtained by dividing the result of subtracting a minimum interval from a maximum interval among the intervals between positive peaks of the blood pressure by the minimum interval; the bio-parameter representing the skin temperature is a SKT indicating an average skin temperature; and the bio-parameters representing the skin resistivity are a skin conductive level (SCL) indicating an average of reciprocals of the values of the skin resistivity, a number of skin conductive response (N-SCR) indicating the number of negative slope zero crossings measured from a graph expressing the reciprocals of the values of the skin resistivity, and skin conductive response magnitude (SCRM) equal to the sum of reciprocals of values of skin resistivity between a negative slope zero crossing and a positive slope zero crossing.

27. The method of claim 26, wherein when the predetermined time is the minimum time, step (d11) comprises the steps of:

(d111) determining whether a HR value decreases by at least a HR threshold value;

(d112) determining whether a SKT value increases by at least a SKT threshold value if it is determined that the HR value decreases by at least the HR threshold value;

(d113) determining whether a LF value decreases by at least a LF threshold value or whether a LF/HF value decreases by at least a LF/HF threshold value if it is determined that the SKT value increases by at least the SKT threshold value;

(d114) determining that probability that the emotional state is happiness is a first predetermined percentage if it is determined that the LF value decreases by at least the LF threshold value or that the LF/HF value decreases by at least the LF/HF threshold value;

(d115) determining whether a RR value increases by at least a RR threshold value and going back to step (d114) if it is determined that the RR value does not increase by at least the RR threshold value; and (d116) determining that probability that the emotional state is happiness is a second predetermined percentage greater than the first predetermined percentage if it is determined that the RR value increases by at least the RR threshold value.

28. The method of claim 27, wherein step (d12) comprises the steps of:

(d121) determining whether the LF value decreases by at least the LF threshold value if it is determined that the SKT value does not increase by at least the SKT threshold value in step (d112); and (d122) determining that probability that the emotional state is stress is the second predetermined percentage if it is determined that the LF value decreases by at least the LF threshold value.

29. The method of claim 28, wherein step (d13) comprises the steps of:

(d131) determining whether the RR value increases by at least the RR threshold value if it is determined that the LF value does not decrease by at least the LF threshold value and that the LF/HF value does not decrease by at least the LF/HF threshold value in step (d113); and (d132) determining that probability that the emotional state is sadness is the second predetermined percentage if it is determined that the RR value increases by at least the RR threshold value.

30. The method of claim 29, wherein step (d14) comprises the steps of:

(d141) determining whether a N-SCR value increases by at least a N-SCR threshold value and whether a SCRM value increases by at least a SCRM threshold value if it is determined that the HR value does not decrease by at least the HR threshold value in step (d111);

(d142) determining whether the SKT value increases by at least the SKT threshold value if it is determined that the N-SCR value increases by at least the N-SCR threshold value and that the SCRM value increases by at least the SCRM threshold value; and (d143) determining that probability that the emotional state is boredom is the second predetermined percentage if it is determined that the SKT value increases by at least the SKT threshold value.

31. The method of claim 30, wherein step (d15) comprises the steps of:

(d151) determining whether the LF/HF value decreases by at least the LF/HF threshold value if it is determined that the SKT value does not increase by at least the SKT threshold value in step (d142) and going back to step (d142) if it is determined that the LF/HF value does not decrease by at least the LF/HF threshold value;

(d152) determining that probability that the emotional state is anger is the first predetermined percentage if it is determined that the LF/HF value decreases by at least the LF/HF threshold value;

(d153) determining whether a SCL value increases by at least a SCL threshold value and going back to step (d152) if it is determined that the SCL value does not increase by at least the SCL threshold value; and (d154) determining that probability that the emotional state is anger is the second predetermined percentage if it is determined that the SCL value increases by at least the SCL threshold value.

32. The method of claim 31, wherein step (d) further comprises the step of determining that no dominant emotional state exists if it is determined that the LF value does not decrease by at least the LF threshold value in step (d121), if it is determined that the N-SCR value does not increase by at least the N-SCR threshold value or that the SCRM value does not increase by at least the SCRM threshold value in step (d141), or if it is determined that the RR value does not increase by at least the RR threshold value in step (d131).

33. The method of claim 26, wherein when the predetermined time is longer than the minimum time, step (d21) comprises the steps of:

(d211) determining whether a RSA value decreases by at least a RSA threshold value, whether a SCL value increases by at least a SCL threshold value, and whether a SCRM value increases by at least a SCRM threshold value;

(d212) determining whether a N-SCR value increases by at least a N-SCR threshold value if it is determined that the RSA value decreases by at least the RSA threshold value, that the SCL value increases by at least the SCL threshold value, and that the SCRM value increases by at least the SCRM threshold value;

(d213) determining whether a SKT value increases by at least a SKT threshold value if it is determined that the N-SCR value increases by at least the N-SCR threshold value;

(d214) determining that probability that the emotional state is boredom is a third predetermined percentage if it is determined that the SKT value increases by at least the SKT threshold value;

(d215) determining whether a HF value decreases by at least a HF threshold value and going back to step (d214) if it is determined that the HF value does not decrease by at least the HF threshold value;

(d216) determining that probability that the emotional state is boredom is a fourth predetermined percentage greater than the third predetermined percentage if it is determined that the HF value decreases by at least the HF threshold value;

(d217) determining whether a LF value decreases by at least a LF threshold value and going back to step (d216) if it is determined that the LF does not decrease by at least the LF threshold value; and (d218) determining that probability that the emotional state is boredom is a fifth predetermined percentage greater than the fourth predetermined percentage if it is determined that the LF decreases by at least the LF threshold value.

34. The method of claim 33, wherein step (d22) comprises the steps of:

(d221) determining that probability that the emotional state is anger is the fifth predetermined percentage if it is determined that the N-SCR value does not increase by at least the N-SCR threshold value in step (d212); and (d222) determining that probability that the emotional state is anger is the third predetermined percentage if it is determined that the SKT value does not increase by at least the SKT threshold value in step (d213).

35. The method of claim 34, wherein step (d23) comprises the steps of:

(d231) determining whether a HR value decreases by at least a HR threshold value if it is determined that the RSA value does not decrease by at least the RSA threshold value, that the SCL value does not increase by at least the SCL threshold value, or that the SCRM value does not increase by at least the SCRM threshold value in step (d211);

(d232) determining whether a RESP value increases by at least a RESP threshold value if it is determined that the HR value decreases by at least the HR value;

(d233) determining that probability that the emotional state is happiness is the third predetermined percentage if it is determined that the RESP value increases by at least the RESP threshold value;

(d234) determining whether a LF/HF value decreases by at least a LF/HF threshold value and going back to step (d233) if it is determined that the LF/HF value does not decrease by at least the LF/HF threshold value;

(d235) determining that probability that the emotional state is happiness is the fourth predetermined percentage if it is determined that the LF/HF value decreases by at least the LF/HF threshold value;

(d236) determining whether the LF value decreases by at least the LF threshold value and going back to step (d235) if it is determined that the LF value does not decrease by at least the LF threshold value; and (d237) determining that probability that the emotional state is happiness is the fifth predetermined percentage if it is determined that the LF value decreases by at least the LF threshold value.

36. The method of claim 35, wherein step (d24) comprises the steps of:

(d241) determining whether the SCL value decreases by at least the SCL threshold value if it is determined that the RESP value does not increase by at least the RESP threshold value in step (d232); and (d242) determining that probability that the emotional state is sadness is the fifth predetermined percentage if it is determined that the SCL value decreases by at least the SCL threshold value.

37. The method of claim 36, wherein step (d25) comprises the steps of:
- (d251) determining whether the N-SCR value increases by at least the N-SCR threshold value if it is determined that the HR value does not decrease by at least the HR threshold value in step (d231); and
- (d252) determining that probability that the emotional state is stress is the fourth predetermined percentage if it is determined that the N-SCR value increases by at least the N-SCR threshold value.

38. The method of claim 37, wherein step (d) further comprises the step of determining that no dominant emotional state exists if it is determined that the SCL value does not decrease by at least the SCL threshold value in step (d241) or if it is determined that the N-SCR value does not increase by at least the N-SCR threshold value in step (d251).

39. The method of claim 22, wherein the reporting the emotional state to the user comprises providing the user with an indication representing the probability of the determined emotional state.

40. The method of claim 22, wherein:
step (d) comprises the steps of:
- calculating an average value of at least one of the extracted bio-parameters;
- determining whether a difference between the average value and a reference value associated with the extracted bio-parameter exceeds a predetermined threshold value; and step (e) comprises the steps of:
- determining the emotional state based on a comparison of the average value and the extracted bio-parameter when the threshold is exceeded; and
- determining the emotional state based on a comparison of the reference value and the extracted bio-parameter when the threshold value is not exceeded.

41. The method of claim 40, wherein the determined emotional state is based on at least two extracted bio-parameters.

42. The method of claim 41, wherein the reporting the determined emotional state to the user comprises providing the user with an indication representing the probability of the determined emotional state.

43. An apparatus for perceiving a physical and emotional state, comprising:
- a bio-signal detection part for attaching to a predetermined portion of a body, and for performing analog signal processing on at least one bio-signal detected from the body and for outputting the processed bio-signal; and
- a bio-signal recognizing part for performing digital signal processing on the processed bio-signal received from the bio-signal detection part, perceiving the physical and emotional state from the result of the digital signal processing, and reporting the physical and emotional state, wherein the reported emotional state comprises an indication representing the probability of the perceived emotional state.

44. A method of perceiving a physical and emotional state, comprising the steps of:
- (a) performing analog signal processing on at least one bio-signal detected from a body; and
- (b) performing digital signal processing on the analog signal processed bio-signal, perceiving the physical and emotional state from the result of the digital signal processing, and reporting the physical and emotional state, wherein reporting the emotional state comprises providing to a user an indication representing the probability of the perceived emotional state.

45. An apparatus for perceiving a physical and emotional state, comprising:
- a bio-signal detection part for attaching to a predetermined portion of a body, and for performing analog signal processing on at least one bio-signal detected from the body and for outputting the processed bio-signal; and
- a bio-signal recognizing part for performing digital signal processing on each processed bio-signal received from the bio-signal detection part, storing at least one reference value associated with the bio-signal, and perceiving the physical and emotional state from the result of the digital signal processing, wherein the bio-signal recognizing part comprises:
  - logical circuitry for calculating an average value of each digital signal processed signal from data previously processed by the bio-signal recognizing part, selecting one of the average value and the reference value based on a difference between the average value and the stored reference value, and for comparing the selected average value or the selected reference value with data currently digitally processed by the bio-signal recognizing part to perceive the physical and emotional state; and
- a reporting mechanism for reporting the physical and emotional state.

46. A method of perceiving a physical and emotional state, comprising the steps of:
- (a) performing analog signal processing on at least one bio-signal detected from a body; and
- (b) performing digital signal processing on the analog signal processed bio-signal, perceiving the physical and emotional state from the result of the digital signal processing, and reporting the physical and emotional state, wherein perceiving the emotional state comprises:
  - calculating an average value of at least one of the digitally processed bio-signals detected from a body;
  - determining whether a difference between the average value and a reference value associated with the digitally processed bio-signal exceeds a predetermined threshold value;
  - perceiving the emotional state based on a comparison of the average value and the digitally processed bio-signal when the threshold is exceeded;
  - perceiving the emotional state based on a comparison of the reference value and the digitally processed bio-signal when the threshold value is not exceeded.

* * * * *